(12) United States Patent
Choi et al.

(10) Patent No.: US 6,416,795 B1
(45) Date of Patent: Jul. 9, 2002

(54) HERBAL EXTRACT COMPOSITION FOR STRESS PREVENTION AND TREATMENT

(75) Inventors: Byung Hag Choi; Gyung Mi Park, both of Seoul (KR)

(73) Assignee: Byung Hak Choi (KR)

( * ) Notice: Subject to any disclaimer, the term of this patent is extended or adjusted under 35 U.S.C. 154(b) by 0 days.

(21) Appl. No.: 09/730,993

(22) Filed: Dec. 6, 2000

(30) Foreign Application Priority Data

Sep. 20, 2000 (KR) .............................................. 00-55082

(51) Int. Cl.⁷ ........................ A01N 65/00; A61K 35/78
(52) U.S. Cl. ....................................... 424/725; 424/773
(58) Field of Search ................................ 424/725, 773

(56) References Cited

U.S. PATENT DOCUMENTS 6,280,751 B1 * 9/2001 Fletcher et al. ............. 424/401

OTHER PUBLICATIONS

Article entitled "Stress" discloses the effects of stress on health in treatments therefor http:/webmd.lycos.com/content/dmk/dmk_summary_account_1466 accessed Nov. 11, 2000.
Article entitled "How Serious is Long–term Stress?" discloses psychological effects http:/webmd.lycos.com/content/dmk/dmk_article_6462848 accessed Nov. 11, 2000.
Article entitled "The Battle To Save Memory", By J.Kluger Time Magazine Oct. 30, 2000 issue.

* cited by examiner

Primary Examiner—Christopher R. Tate
Assistant Examiner—Patricia Patten
(74) Attorney, Agent, or Firm—Bachman & LaPointe, P.C.

(57) ABSTRACT

The present invention provides antistress compositions containing various medicinal herbs which are composed of one or more medicinal herbs 2.0–40.0 g of *fructus hordei germintus, messa medicata fermentata, fructus amomi* and *fructus crataegei*; one or more medicinal herbs 2.0–40.0 g of *radix polygalae, semen zizyphi spinosae* and *rhizoma acori graminei*; one or more medicinal herbs 2.0–40.0 g selected from the group consisting of *poria holen* and *poria*, one or more medicinal herbs 2.0–40.0 g of *folium phyllostachys*, calus in *taein phyllostachys, succus phyllostachys* and *radix scutellariae*; one or more medicinal herbs 2.0–40.0 g of germinated *Glycine max (L.) Merr, fructus amomicardamomi, semen glycine* and *semen lablab*; one or more medicinal herbs 2.0–40.0 g of *rhizoma zingiberis, radix asari, rhizoma zingiberis siccatum* and *radix aconiti*; one or more medicinal herbs 2.0–40.0 g of *bulbos allii fistulosi, herba ephedrae* and *folium perillae*; and one or more medicinal herbs 2.0–40.0 g of *red pepper* and *radix platycodi* as the effective ingredients that relieve stress and repress memory failure.

12 Claims, 1 Drawing Sheet

FIG. 1

HERBAL EXTRACT COMPOSITION FOR STRESS PREVENTION AND TREATMENT

FIELD OF THE INVENTION

The present invention relates to an antistress composition containing various medical herbs as effective ingredients that relieve stress and repress memory failure.

Particularly, the present invention relates to an antistress composition containing mixture which is composed of one or more medicinal herbs 2.0–40.0 g selected from the group consisting of *fructus hordei germintus, messa medicata fermentata, fructus amomi* and *fructus crataegei*; one or more medicinal herbs 2.0–40.0 g selected from the group consisting of *radix polygalae, semen zizyphi spinosae* and *rhizoma acori graminei*; one or more medicinal herbs 2.0–40.0 g selected from the group consisting of *poria holen* and *poria*; one or more medicinal herbs 2.0–40.0 g selected from the group consisting of *folium phyllostachys*, calus in *taein phyllostachys, succus phyllostachys* and *radix scutellariae*; one or more medicinal herbs 2.0–40.0 g selected from the group consisting of germinated *Glycine max (L.) Merr, fructus amomicardamomi, semen glycine* and *semen lablab*; one or more medicinal herbs 2.0–40.0 g selected from the group consisting of *rhizoma zingiberis, radix asari, rhizoma zingiberis siccatum* and *radix aconiti*; one or more medicinal herbs 2.0–40.0 g selected from the group consisting of *bulbos allii fistulosi, herba ephedrae* and *folium perillae*; and one or more medicinal herbs 2.0–40.0 g selected from the group consisting of red pepper and *radix platycodi* as the effective ingredients.

The antistress composition of the present invention is so effective for stress relief and memory failure repression that they can be useful for preventing and treating stress and memory failure. The composition can be also used in a form of health food.

BACKGROUND

Generally, overloaded stimulus may result in injury to a living body. At this time, the living body exposed to the overloaded stimulus shows a general adaptive syndrome as a reaction to a certain threat irrelevant to the kind of stimulus, and this phenomena has been defined as a stress (Selye, H: The stress of life, Toronto, Longnans Green and Co., pp.1–50, 1958).

This reaction is represented as the various phenomena in the body, which develop strain headache, migraine, hypertension, dyspepsia, fatigue, pain, climacteric suffering, hair growing and rough skin. If these phenomena continue chronically, neuropathy and stomach ulcer are caused and physiological activity and immune response are reduced. It also threatens the health considerably since the breakage of homeostasis in the body weakens resistance, and then causes other disease. In addition, it shrinks psychological activity and induces abnormal behavior because of instable emotion. Particularly, the stress is raised as a very important problem since it is excessively occurred in the modern society.

The stress which is called as the root of modern diseases is induced by various causes:

1) Physical factor—overexertion, lack of sleep, external wound, addiction, etc.
2) External factor—natural environment, cultural state, human relationship in the home or in the office, etc.
3) Internal factor—personality, mental conflict in the real life, mental injury in the childhood, etc.

The effect of this stress to the human body is so various that it induces nervousness, headache, hypertension, etc, and the continued stress decreases the function of the body such that it may cause other secondary diseases. As the above-mentioned, the cause of the stress is various according to the method which inflicts injury to the body, but it is commonly said that all the following reactions are mediated by accelerating the function of HPA, sympathetic nervous system, which induces hormone secretion. These reactions can be summarized as follows. Adrenal gland which is stimulated by adrenal corticotropic hormone increases its weight and decreases the lipid, and the spleen considerably decreases its weight because of the decline of immune function. On the other hand, adrenal gland increases cholesterol, blood sugar, alkaline phosphatase(ALP), lactate dehydrogenase(LDH), aspartate aminotransferase(AST or GOT), alanine aminotransferase(ALT or GPT) by secreting other steroid hormone and induces the decrease of neutral lipid in case of serious state. These variations in the living body are reported as the middle step of external symptoms which are above-mentioned. Therefore, to prevent or cure the stress, it is desirable to recover diverse physiological variations in the human body occurred by the stress.

The variations which are induced by the stress are very diverse and if these states are continued, it becomes the root of many diseases. So it is urgently necessary to relieve the stress. However, only the physical treatment methods like sports, sleeping and relaxation have been suggested. The methods which stimulate recovery of physiological variations induced by the stress have been poorly suggested. Therefore, development of the medicine which has the preventive and curing effect to the stress has been demanded.

As part of these researches, antistress agents containing cholic acids have been developed (Korea patent No.95-6225). The antistress agents include cholic acids which are widely used as a solubilizing agent of gallstone. Since the antistress agents have the activity of choleretic function, liver detoxification, improvement of liver blood stream, stimulating function of lipid absorption and waste excretion through fine biliary duct, they are marketed as the gallstone solubilizer. They also contain ursodeoxycholic acid which has the effects of liver function improvement in chronic liver disease, general malaise by the liver function disturbance, dyspepsia, anorexia and body fatigue; tauroursodeoxycholic acid effective for liver lipid treatment (JP No.4-235918) which is reported to improve liver function and decrease the amount of liver lipid by oral administration; chenodeoxycholic acid and dehydrocholic acid that are on sale as solubilizing agents of gallstone.

However, the antistress compositions have been proved to be effective only for weight increase of adrenal gland and shrink of spleen, and has the repressive effects for ascorbic acid content variation of adrenal gland and blood biochemical variation which are general symptoms induced by the stress. So it is not mentioned at all about the effect which represses or recovers memory failure induced by the stress.

Moreover, various forms of medicines principally made from ginseng, Eucommiaceae ulmoides, brekman that are reported to be useful for the stress as amedicinal herb or a folk remedy, are developed (Korea patent No.96-8230). The nutrition tonic containing ginseng as a principal ingredient is widely marketed, and the nutrition tonic containing Eucommiaceae ulmoides as a principal ingredient is marketed. In addition, the nutrition tonic comprised of various compounds like honey, vitamin and the like is marketed. However, though it is reported that the medicinal herbs like ginseng, brek-hman(Pharmacological investigation of glycosides from Gingseng and Eleutherococcus, Loydia, Vol.32, No.1, pp.46–51, 1969), ocimum sanctum Linn, tinosporamalabarica(Sen, P., Maiti, PC and Ray, A. Mechanism of anti-stress activity of Linn, eugenol and in experimental animals, Indian J. Exp. Biol., 30, 592–596, 1992) and biological materials. like melatonin have the antistress function, they have the effect. to the only small part of diverse variations which are induced by the stress or have a little effect. In addition, they have no unique characteristic in the point of using the medicinal herb extracts which have been used as traditional oriental material and generally, they have only the purpose using the nutrition tonic or commonly known effect.

Therefore, it is asked for the development of desirable antistress agents which have the repressive effects to the various symptoms induced by the stress.

As a result of much effort to develop new antistress agents which have excellent effect and have not been used in combination so far, the present inventors have developed an antistress composition containing *fructus hordei germintus, radix polygalae, poria holen, folium phyllostachys, germinated Glycine max (L.) Merr, rhizoma zingiberis, bulbus allii fistulosi* and *red pepper* as effective ingredients, and verified that the antistress composition had wide and excellent effect on the prevention and cure of stress and memory failure.

SUMMARY OF THE INVENTION

It is an object of this invention to provide an antistress composition containing various medicinal herbs as effective ingredients to relieve stress and memory failure.

It is another object of this invention to provide an antistress composition containing mixture composed of *fructus hordei germintus, radix polygalae, poria holen, folium phyllostachys, germinated Glycine max (L.) Merr, rhizoma zingiberis, bulbus allii fistulosi* and *red pepper* which have the effects on relief of stress and repression of memory failure induced by excessive stress.

In accordance with the present invention, the foregoing objects and advantages are readily accomplished by the provision of an antistress composition containing mixture which is composed of one or more medicinal herbs 2.0–40.0 g selected from the group consisting of *fructus hordei germintus, messa medicata fermentata, fructus amomi* and *fructus crataegei*; one or more medicinal herbs 2.0–40.0 g selected from the group consisting of *radix polygalae, semen zizyphi spinosae* and *rhizoma acori graminei*; one or more medicinal herbs 2.0–40.0 g selected from the group consisting of *poria holen* and *poria*; one or more medicinal herbs 2.0–40.0 g selected from the group consisting of folium phyllostachys, calus in taein phyllo-stachos, succus phyllostachys and radix scutell-ariae; one or more medicinal herbs 2.0–40.0 g selected from the group consisting of *germinated Glycine max (L.) Merr, rhizoma zingiberis, fructus amomicardamomi, semen glycine* and *semen lablab*; one or more medicinal herbs 2.0–40.0 g selected from the group consisting of *rhizoma zingiberis, radix asari, rhizoma zingiberis siccatum* and *radix aconiti*; one or more medicinal herbs 2.0–40.0 g selected from the group consisting of *bulbos allii fistulosi, herba ephedrae* and *folium perillae*; and one or more medicinal herbs 2.0–40.0 g selected from the group consisting of *red pepper* and *radix platycodi* as the effective components.

This invention also provides a pharmaceutical composition containing the antistress compositions as the effective ingredients which has preventive and curing effects on the stress.

In addition, the present invention provides health food containing the antistress agent as an effective ingredient which has preventive and curing effects on the stress.

DETAILED DESCRIPTION OF PREFERRED EMBODIMENTS

Hereinafter, the present invention will be described in detail.

The present invention provides an antistress composition containing various medical herbs as effective ingredients that relieve stress and repress memory failure.

The antistress composition of the present invention contains mixture which is composed of one or more medicinal herbs 2.0–40.0 g selected from the group consisting of *fructus hordei germintus, messa medicata fermentata, fructus amomi* and *fructus crataegei*; one or more medicinal herbs 2.0–40.0 g selected from the group consisting of *radix polygalae, semen zizyphi spinosae* and *rhizoma acori graminei*; one or more medicinal herbs 2.0–40.0 g selected from the group consisting of *poria holen* and *poria*, one or more medicinal herbs 2.0–40.0 g selected from the group consisting of *folium phyllostachys,* calus in *taein phyllostachys, succus phyllostachys* and *radix scutellariae*; one or more medicinal herbs 2.0–40.0 g selected from the group-consisting of *germinated Glycine max (L.) Merr, fructus amomicardamomi, semen glycine* and *semen lablab*; one or more medicinal herbs 2.0–40.0 g selected from the group consisting of *rhizoma zingiberis, radix asari, rhizoma zingiberis siccatum* and *radix aconiti*; one or more medicinal herbs 2.0–40.0 g selected from the group consisting of *bulbos allii fistulosi, herba ephedrae* and *folium perillae*; and one or more medicinal herbs 2.0–40.0 g selected from the group consisting of *red pepper* and *radix platycodi* as the effective components.

*Fructus hordei germintus* is acquired by sprouting annual medicinal herb, barley, easily regarded as Korean traditional food which is called as malt, but it is the enzyme acquired from the nature and used universally. *Fructus hordei germintus* is the bud which is germinated by relevant watering and at regular temperature, and it contains a lot of amylase. Using the function of amylase, it is used to manufacture fermented rice punch, rice nectar, glutinous starch syrup, taffy, beer and the like. Well-made *fructus hordei germintus* contains protease, invertase, oxidative enzyme, phytase other than amylase. Of the amylase, it is the α-amylase that is comprised a lot in *fructus hordei germintus* but the β-amylase that is not almost comprised. In addition, the protease of *fructus hordei germintus* has the effect which makes the flavor, the taste and the foam better by degrading the protein.

*Fructus hordei germintus* is used as follows. *Fructus hordei germintus* is soaked in water, is taken out of water, is put in a roub basket and the top is weaved by a cattail, in the state of covering with a buddle, is frequently watered and germinated below 60° C. and is collected and dried under the sun when the length of the bud becoms about 3–5 cm.

*Fructus hordei germintus* has the effect to the cure of acute and chronic hepatitis, stimulates an appetite, represses an intestinal convulsion and cures dyspepsia, vomiting, diarrhea and the like. It is preferable that the antistress components of the present invention to contain 2.0–40.0 g of *fructus hordei germintus*.

As an alternative medicinal herb of *fructus hordei germintus*, *messa medicata fermentata*, *fructus amomi* and *fructus crataegai* can be used.

*Radix polygalae* is the part of root of the perennial medicinal herb which is belong to *radix polygalae* family. The part of the root contains a lot of saponin, and saponin is hydrolyzed to crystal of tenuiginin A and tenuiginin B. In addition, it contains polygalitol, N-acetylglycosamine, alkaloid tenuidine, vegetable fat, resin and the like. Since plant saponin which is comprised in *radix polygalae* induces light vomiting by stimulating stomach mucosa, it has the effects of discharging phlegm by increasing an exudate in bronchus and RBC hydrolysis. It has been reported that the herb tea of *radix polygalae* induces exciting effect for guinea pig, rabbit, unpregnented dog and the removed womb of pregnented dog.

*Radix polygalae* is used as follows. The root of *radix polygalae* is collected in spring and summer. The pith of the inner part is removed, and then, the pith-removed *Radix polygalae* is soaked in *Glycyrrhiza uralens* is Fish-extracted water for about 15–20 min and is dried in the shade.

*Radix polygalae* has the effects which stabilize mentality, make brain fresh, and discharge phlegm and congestion of blood. In addition, it has the functions which increase wisdom, make the health and eyesight better and reinforce memory. It is preferable for the antistress agent of the present invention to contain 2.0 g–40.0 g of *radix polygalae*.

As an alternative medicinal herb of *radix polygalae*, *semen zizyphi spinosae* and *rhizoma acori graminei* can be used.

*Poria holen* is the white part which contains naturally pine root in the middle of stem-and the part of the root of the plant belonging to Polyporaceae family. *Poria holen* tastes sweet and flat, has ordinary property and it has been reported that *poria holen* generally stabilizes mentality, excretes water and treats worry susceptibility to fright, amnesia, insomnia, epilepsy, urine handicap and the like. If *poria holen* has been injected to the intestine of experimental animal which is excited state by taking caffeine, experimental animal is stabilized to the state of dozing but does not show sleeping phenomena.

*Poria holen* is collected in spring or summer, dried in the shade and used as medicinal herb. It is preferable for the antistress agent of the present invention to contain 2.0 g–40.0 g of *poria holen*.

As an alternative medicine of *poria holen*, poria can be used.

*Folium phyllostachuos* is the leaflet of the black bamboo belonging to rice family, contains arundoin, cylindrin, taraxelrol and fridelin, which are triterpenoid compound, and, in addition, contains phenol-based lipid, amino acid, organic acid, saccharide and the like. *Folium phyllostachys* tastes sweet and flat, has cold property, cures symptoms of swollen and painful gingiva, gets rid of the thirst of a fever, discharges urine well and makes mental refreshing. In addition, folium phyllostachys discharges phlegm, makes eyes bright and temperature go down and has the effect of detoxification. In case of oral administration to the rat which is artificially developed fever, it has been reported that it shows excellent alleviation of a fever and has urination function by increasing chloride excretion.

*Folium phyllostachys* is collected as the leaflet of the black bamboo in May-June before blooming, is dried in the sun and is used as medicinal herb. *Folium phyllostachys* alleviates fever, makes urination better, makes eyes bright and treats symptoms of swollen and painful gingiva and mouth inflammation. It is preferable for the antistress agent of the present invention to contain 2.0–40.0 g of *folium phyllostachys*.

As an alternative medicinal herb of *folium phyllostachys*, calcus in taein phyllostachys, *succus phyllostachys* and *radix scutellarial* can be used.

*Germinated Glycine max (L.) Merr* is germinated black soybean belonging to Leguminosae family and generally means bean sprouts. Although bean sprouts is the food which is made of germinated soybean, it is better to ingest bean sprouts rather than to ingest soybean and has the effects for cure and prevention of the various adult diseases. The remarkable thing in the bean sprouts is that it produces vitamin C, vitamin $B_2$, niacin and vitamin K which are absent in ingeminated black soybean. In addition, it is estimated as the important source of vitamins and minerals in North Europe since it contains a lot of minerals like potassium and calcium and food fibers. The digestive absorption rate of soybean itself is low, but soybean sprouts has high digestive absorption rate since it contains digestive enzymes such as amylase, invertase and the like and comprises lysine, tryptophan, methionine and the like as vegetable protein. In addition, green-bean sprouts and mung bean sprouts have a lot of phosphorous and vitamin $B_2$, but since the components are easily soluble in water, they should be eaten by roasting in oil. Soybean sprouts which has low calorie and large volume is very popular for diet food and is reported that they promote health by the much intake of food fiber if they are cooked with other vegetables.

*Germinated Glycine max (L.) Merr* is that domestic yellow soybean for the use of soybean sprouts is germinated by soaking in water, is grown at ambient temperature for about 5 days, is completely dried in the cold place and is used as medicinal herb.

*Germinated Glycine max (L.) Merr* vitalizes the body mentally and physically and cures lingering intoxification, headache and stomachache which are induced by a cold, diarrhea, skin disease. It is preferable that the antistress components of the present invention contain 2.0–40.0 g of germinated *Glycine max (L.) Merr*.

As an alternative medicinal herb, *fructus amomi cardamomi*, *semen glycine* and *semen lablab* can be used.

*Rhizoma zingiberis* is perennial medicinal herb belonging to ginger family, is used as a source without asking irrespective of the East and the West and has the big effect not only to the flavor but also to the health. Particularly, *rhizoma zingiberis* shows the effect of the resistance to the ulcer and contains the same components of the gastric ulcer drug which is marketed now. The mixture of 6-gingetol and 26-gingetol which are oil components of the pungent taste of *rhizoma zingiberis* increases bile secretion which stimulates digestive absorption of lipid at about 1.3 fold. In addition, *rhizoma zingiberis* represses sickening and vomiting, is helpful to prevent constipation by increasing the intestinal activity, makes intestine clean and stops diarrhea. On the other way, it has been reported that *rhizoma zingiberis* alleviates pain, shows cough remedy, and sterilizes anisakis which is parasitic in sashimi and shakes intestine violently. *Rhizoma zingiberis* is a natural medicinal herb which has strong antioxidative function such as vitamin E, vitamin C, betacarotene, green tea shows that the effect of each component, in the view of experiment, is the same as or stronger than synthetic drug and may show synergy effect with other component and has no side effect.

*Rhizoma zingiberis* is picked in spring and is used as medicinal herb after *rhizoma zingiberis* removed of stem, leaf and hair root is washed clean. *Rhizoma zingiberis* acts on digestive system, stops vomiting, discharges phlegm, induces excitement function to the center of blood vein activity and respiration and has the effects of antibacteria and antiprotozoan. It is preferable for the antistress agent of the present invention to contain 2.0–40.0 g of *rhizoma zingiberis*.

As an alternative medicinal herb, *radix asari, rhizoma zingiberis siccatum* and *radix aconiti* can be used.

*Bulbus allii fistulosi* is the perennial medicinal herb, the leek belonging to a lily family and is reported as panacea of tonsils, headache, kidney disease, cold, nervous breakdown, insomnia, fever and diarrhea. In our country, the leek is used only as food source but it has been developed as medicine.

The pungent component of the leek is allyl sulfide, which exists glycoside form in the organism and which is produced by the enzyme of disrupted cell and is evaporated by heat. The leek contains a lot of water but it contains a lot of amino acids in dried state which contain 30% alanine that degrades lipid, recovers fatigue and increases mental power and 30% glutamine that helps lipid metabolism, detoxificates harmful material and stimulates brain development. So the leek has been analyzed to have the effect not only for food but also for circulatory system disease like cerebral apoplexy as a medicine.

*Bulbus allii fistulosi* is used as a medicinal herb which is dried in the shade after washing the leek which is removed of soil. *Bulbus allii fistulosi* cures heat and cold, headache, stomachache, bad urination and defecation, dysentery, swell and cleans the large and small intestinal convulsion and beriberi. It is preferable for the antistress agent of the present invention to contain 2.0–40.0 g of *bulbus allii fistulosi*.

As an alternative medicinal herb, *herba ephedrae* and *folium perillae* can be used.

*Red pepper* which contains capsaicin tastes pungent, contains carotene of pigment component, which oxidizes to capsanthin when green pepper matures and becomes *red pepper* of deep red. If capsaicin is moderately ingested, it has the effects of promotion of appetite, keeping warmth and sterilization of intestine. The people who live in hot weather eat *red pepper* as the source of power and the people who live in cold weather eat *red pepper* for the purpose of making the body warm.

In oriental medicine, *red pepper* has the function of making eyesight better, helps digestion by activating stomach, is introduced as folk remedy which helps blood stream by retaining heat, relieve the pain of neuralgia or arthritis by cauterizing with powdered *red pepper* in folk remedy and cures gout or arthritis. In addition, *red pepper* has the functions of removal of pain and promotion of metabolism.

*Red pepper* is collected in autumn when it ripens and used as medicinal herb after it is dried in the sun and is cleaned with dried towel. It is preferable for the antistress agent of the present invention to contain 2.0–40.0 g of *red pepper*.

As an alternative medicinal herb, *rhizoma zingiberis* and *radix platycodi* can be used.

In addition, the present invention provides a pharmaceutical composition which comprises the antistress compounds as the effective ingredients and have the effects for stress prevention and treatment.

The antistress agent of the present invention can be prepared by customary method which is known in this field and can be formulated into herb tea (infusion), pill, tablet, soft capsule, liquid, powder and granule.

In general, the herb tea is called as whole medicinal decoction and is the type of liquid medicine. The herb tea can be prepared by the following method; mixture of the medicinal herbs mentioned in the above is soaked in water, heated for a certain time, and then dregs is discarded in order to obtain water extract. The herb tea is widely used type of oriental medicine and has many advantages, for example, easy absorption, rapid treatment and simple preparation. It is desirable to use the utensil of porcelin or enamel which is made of soil. This can reduce denaturation of tanin and organic acids which is contained in the medicinal herbs, and thus increase the medicinal effect. So it is undesirable to use the utensil of iron or copper.

In addition, it is desirable to use white cotton cloth as the herb tea pocket which is used when the medicinal herbs are boiled down in an extractor, since it does not make chemical reaction and filters fine dregs well comparatively.

Then, the liquid component of the herb tea extracts is packed in a vacuum by using automatic package machine in order to drink easily by the amount of one time.

On the basis of the customary preparing method, the preparing method of the antistress components in the present invention is composed of the following steps;

1) soaking a mixture of the medicinal herbs comprised of *fructus hordei germintus* 2.0–40.0 g, *radix polygalae* 2.0–40.0 g, *poria. holen* 2.0–40.0 g, *folium phyllostachys* 2.0–40.0 g, germinated *Glycine max (L.) Merr* 2.0–40.0 g and *rhizoma zingiberis* 2.0–40.0 g in water;

2) putting the soaked medicinal herbs of the step 1 into a pocket in order to obtain a water extract and adding the obtained water extract with *bulbos allii fistulosi* 2.0–40.0 g and *red pepper* 2.0–40.0 g into a water-containing, preheated extractor in order to obtain a herb tea; and, 3) moving the extracted herb tea of the step 2 to a automatic package machine and packing the extracted herb tea in a predetermined amount with the automatic package machine.

It is proper to soak the medicinal herbs of the step 1 for about 30 min to 1 hour, which makes the effective ingredients of the medicinal herbs solubilized easily.

It is desirable to use white cotton cloth for the pocket in the step 2 and the herb tea is extracted by boiling for about one and a half hour after adding water 4000 cc per dried medicinal herb 500 g.

In the step 3, transference of the extracted herb tea from the extractor to the packaging machine can be achieved by the assistance of suddenly increased pressure. During this happens, dregs remain in the extractor.

Pills are the types of various granules which are made by adding paster to the fine powder of medicinal herb, and honey pill, water pill and oil pill are generally used in clinic. Pills provide simple intake, gentle absorption, long continuance and convenient carry and store.

The preparing method of the pills of the antistress agent of the present invention is composed of the following steps;

1) preparing a mixture of medicinal herbs by mixing and powdering *fructus hordei germintus* 2.0–40.0 g, *radix polygalae* 2.0–40.0 g, *poria holen* 2.0–40.0 g, *folium phyllostachys* 2.0–40.0 g, *germinated Glycine max (L.) Merr* 2.0–40.0 g, *rhizoma zingiberis* 2.0–40.0 g, *bulbos allii fistulosi* 2.0–40.0 g and *red pepper* 2.0–40.0 g;
2) slowly heating honey until the honey becomes yellow after heating and filtering the honey for several times;
3) adding the mixture of medicinal herbs of the step 1 to the hot honey and kneading the medicinal herbs-added honey into dough;
4) molding the dough of the step 3 into pill of a predetermined size with artificial or pill machine;
5) sealing up and storing the pill of the step 4 in the shaded and cold place after drying in the cold and dried place In the step 1, after powdering all the components of medicinal herbs, they are all added and pulverized repeatedly in the blender for several times in order to mix each medicinal herb evenly.

In the step 2, honey is prepared for 250 cc per pulverized medicinal herb 500 g and water, walnut oil and vinegar can be used instead of the honey. The honey is heated until it is sticky and has yellow fiber when picked and rubbed with finger and it isn't sticky in the palm.

The capsule of the antistress agent of the present invention is prepared by lyophilizing the herb tea which is prepared in the above-mentioned method, and followed by putting an appropriate amount into the capsule.

On the other hand, the pharmaceutical composition of the present invention can be prepared to the customary drug type by adding one or more pharmaceutically acceptable carriers and one or more additives to an effective amount of the antistress agent.

Carrier can be selected from one or more of diluent, glosser, binder, vehicle, sweetening agent, stabilizer and antiseptic, and additive can be selected from one or more of spice, vitamins and antioxidant. The composition of the present invention can be prepared in the type of herb tea, pill, tablet, capsule, soft capsule, liquid, granule and powder, and can be orally administered.

In the present invention, any pharmaceutically acceptable carrier and additive can be used. Particularly, diluent can be selected from the group consisting of lactose monohydrate, cornstarch, soybean oil, microcrystalline cellulose and D-mannitol. Glosser is preferable to be selected from magnesium stearate or talc, and binder from polyvinylpyrrolidone(PVP) or hydroxypropylcellulose (HPC). In addition, it is desirable to select calcium carboxymethylcellulose, sodium starch glycolate, polacrylin potassium or cross-linked polyvinylpyrrolidone as the vehicle, white sugar, fructose, sorbitol or aspartam as the sweetening agent, sodium carboxymethylcellulose (Na-CMC), beta-cyclo-dextrin, white bee's wax or xanthan gum as the stabilizer, methylparaben, propylparaben or potassium sorbate as the antiseptic.

In the pharmaceutical compositions of the present invention except the main components above, mineral compounds of vitamin B, C, E or beta-carotene, Ca, Mg, Zn or phosphlipid like lecitin or maltol and amino acids compounds can be used as the auxiliary component and it is preferable to use the mixture of 2–3 components of vitamin C, E or beta-carotene, and maltol because of increasing or reinforcing biological activity.

In addition to the preceded components, as the known additive, the natural spices or natural juices like Japanese apricot, lemon, pineapple or herb; natural pigments of chlorophyllin and flavonoid; sweetening components of fructose, honey, sugar alcohol, sugar; and souring components like citric acid and sodium citric acid can be used in order to promote appetite.

The antistress composition of the present invention can be orally administered in an amount of 30–120 g/day, preferably 40–60 g/day based on 60 kg adult in the type of herb tea, pill, tablet, capsule, soft capsule, liquid, granule or powder.

Since the antistress composition of the present invention contains the medicinal herbs widely used in the oriental medicine and toxicity data thereof are well-known, therefore, acute toxicity test have not been performed.

In addition, the present invention provides health food which has preventive and curing effect for stress, which comprises the antistress composition as the effective ingredients.

The health food comprising the antistress components of the present invention are folk remedies of tea, jelly, juice and drink containing the medicinal herbs as the effective ingredients for the purpose of prevention of stress and repression of memory failure.

The present inventors have confirmed that the antistress composition of the present invention has an effect on the prevention and treatment of stress and memory failure by the animal test: The herb tea extracts of the antistress composition of the present invention were administered and the stress was given to the experimental animals which were educated by Morris water maze test. The time to get to the objective place and the variation of a time to find out the point were measured. As a result, in the normal state, the experimental animals memorized the objective place where they were educated for 20 times after 6 weeks, but their educated memory was declined very much because of the external physical stress. However, these phenomena of memory failure were repressed by the herb tea which was injected with the external physical stress. So, it was confirmed that the herb tea extracts of the antistress composition of the present invention had the effects on preventing memory failure and recovering memory power.

To put together the results, it has been demonstrated that the herb tea extracts of the present invention, which are administered to the experimental animals, have the effects of preventing the failure of education ability and memory power and recovering memory power since the antistress composition of the present invention has the synergetic effect by combining the above mentioned medicinal herbs.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Pharmaceutical Compositions of Antistress Agents; Herb Tea

<1–1>

In order to prepare a herb tea-type pharmaceutical composition comprising the antistress components of the present invention as the effective ingredients, after weighing *fructus hordei germintus* 5.0 g, *radix polygalae* 3.0 g, *poria holen* 3.0 g, *folium phyllostachys* 3.0 g, *germinated Glycine max (L.) Merr* 3.0 g, *rhizoma zingiberis* 2.0 g, *bulbos allii fistulosi* 2.0 g and *red pepper* 2.0 g on a balancer, the rest medicinal herbs except *red pepper* and *bulbos allii fistulosi* were soaked in water to decoct the effective ingredients of the medicinal herbs for about 30 min or 1 hour.

After the medicinal herbs soaked in water, they were collected in a pocket, and *red pepper* and *bulbos allii fistulosi* were added, the herb tea were extracted by boiling down in a preheated herb tea extractor. At this time, it was preferable to use the pocket made of white cotton cloth. The herb tea were extracted by adding water 4000 cc to dried medicinal herbs 500 g and boiling for about one and a half hour.

In order to move the extracted herb tea like the preceded method, after the pressure of the extractor was suddenly increased, the extracted herb tea was moved to a package machine by opening the valve for the automatic package machine, and packaged for the dosage of one time and the dregs were left in the extractor.

<1–2>

The herb tea was prepared by using *fructus hordei germintus* 20.0 g, *radix polygalae* 16.0 g, *poria holen* 16.0 g, *folium phyllostachys* 16.0 g, *germinated Glycine max (L.) Merr* 15.0 g, *rhizoma zingiberis* 10.0 g, *bulbos allii fistulosi* 10.0 g and *red pepper* 8.0 g as the medicinal herbs of antistress components via the procedure described in the Example <1–1>.

<1–3>

The herb tea was prepared by using *hordei germintus* 20.0 g, *semen zizyphi spinosae* 16.0 g, *poria holen* 16.0 g, calcus in *taein phyllostachys* 16.0 g, *germinated Glycine max (L.) Merr* 15.0 g, *radix asari* 10.0 g, *bulbos allii fistulosi* and *radix platycodi* 8.0 g as the medicinal. herbs of antistress components via the procedure described in the Example <1–1>.

<1–4>

The herb tea was prepared by the preceded (step 1) and the medicinal herbs of antistress components were *messa medicata fermentata* 20.0 g, *radix polygalae* 16.0 g, *poria* 16.0 g, *folium phyllostachys* 16.0 g, *fructus amomicardamomi* 15.0 g, *rhizoma zingiberis* 10.0 g, *herba ephedrae* 10.0 g and *red pepper* 8.0 g.

<1–5>

The herb tea was prepared by using *messa medicata* 20.0 g, *semen zizyphi spinosae* 16.0 g, *poria* 16.0 g, calcus in *taein phyllostachys* 16.0 g, *fructus amomicardamomi* 15.0 g, *radix asari* 10.0 g, *herba ephedrae* 10.0 g and *radix platicodi* 8.0 g as the medicinal herbs of antistress components via the procedure described in the Example <1–1>.

<1–6>

The herb tea was prepared by using *fructus amomi* 20.0 g, *rhizoma acori graminei* 16.0 g, *poria* 16.0 g, *succus phyllostachys* 16.0 g, *semen glycine* 15.0 g, *rhizoma zingiberis siccatum* 10.0 g, *folium perillae* 10.0 g and *radix platycodi* 8.0 g as the medicinal herbs of antistress components via the procedure described in the Example <1–1>.

<1–7>

The herb tea was prepared by using *fructus crataegei* 20.0 g, *semen zizyphi spinosae* 16.0 g, poria holen 16.0 g, *radix phyllostachys* 16.0 g, *semen lablab* 15.0 g, *radix aconiti* 10.0 g, *folium perillae* 10.0 g and *radix platycodi* 8.0 g as the medicinal herbs of antistress components via the procedure described in the Example <1–1>.

Example 2

Preparation of Pharmaceutical Compositions of Antistress Agents; Tablet

<2–1>

In order to prepare a tablet-type pharmaceutical composition comprising the antistress components of the present invention as the effective ingredients, after weighing *fructus hordei germintus* 5.0 g, *radix polygalae* 3.0 g, *poria holen* 3.0 g, *folium phyllostachys* 3.0 g, *germinated Glycine max (L.) Merr* 3.0 g, *rhizoma zingiberis* 2.0 g, *bulbos allii fistulosi* 2.0 g and *red pepper* 2.0 g on a balancer, the mixture of medicinal herbs were prepared by pulverizing each medicinal herb finely and mixing evenly. At this time, after pulverizing the each component of medicinal herb, each medicinal herb was evenly mixed by repeating pulverization of all the powder in a blender for several times.

After repeatedly heating and filtering of the honey which was prepared for 250 cc per pulverized medicinal herb 500 g three or four times, it was heated until the honey was sticky, had yellow fiber when picked and rubbed with finger and wasn't sticky in the palm. Water, walnut oil and vinegar could be used instead of the honey. After kneading the mixture of the medicinal herbs by adding the hot honey which was prepared like this, the pill was prepared by molding the kneading into the regular size using artificial or pill machine. The pill was sealed up and stored in the shaded and cold place after drying in the cold and dried place.

<2–2>

The pill was prepared by using *fructus hordei germintus* 20.0 g, *radix polygalae* 16.0 g, *poria holen* 16.0 g, *folium phyllostachys* 16.0 g, *germinated Glycine max (L.) Merr* 15.0 g, *rhizoma zingiberis* 10.0 g, *bulbos allii fistulosi* 10.0 g and *red pepper* 8.0 g as the medicinal herbs of antistress components via the procedure described in the Example <2–1>.

<2–3>

The pill was prepared by using *hordei germintus* 20.0 g, *semen zizyphi spinosae* 16.0 g, *poria holen* 16.0 g, calcus in *taein phyllostachys* 16.0 g, *germinated Glycine max (L.) Merr* 15.0 g, *radix asari* 10.0 g, *bulbos allii fistulosi* and *radix platycodi* 8.0 g as the medicinal herbs of antistress components via the procedure described in the Example <2–1>.

<2–4>

The pill was prepared by using *messa medicata fermentata* 20.0 g, *radix polygalae* 16.0 g, *poria* 16.0 g, *folium phyllostachys* 16.0 g, *fructus amomicardamomi* 15.0 g, *rhizoma zingiberis* 10.0 g, *herba ephedrae* 10.0 g and *red pepper* 8.0 g as the medicinal herbs of antistress compnents via the procedure described in the Example <2–1>.

<2–5>

The pill was prepared by using *messa medicata* 20.0 g, *semen zizyphi spinosae* 16.0 g, *poria* 16.0 g, calcus in *taein phyllostachys* 16.0 g, *fructus amomicardamomi* 15.0 g, *radix asari* 10.0 g, *herba ephedrae* 10.0 g and *radix platicodi* 8.0 g as the medicinal herbs of antistress components via the procedure described in the Example <2–1>.

<2–6>

The pill was prepared by using *fructus amomi* 20.0 g, *rhizoma acori graminei* 16.0 g, *poria* 16.0 g, *succus phyllostachys* 16.0 g, *semen glycine* 15.0 g, *rhizoma zingiberis siccatum* 10.0 g, *folium perillae* 10.0 g and *radix platycodi* 8.0 g as the medicinal herbs of antistress components via the procedure described in the Example <2–1>.

<2–7>

The pill was prepared by using *fructus crataegei* 20.0 g, *semen zizyphi spinosae* 16.0 g, *poria holen* 16.0 g, *radix phyllostachys* 16.0 g, *semen lablab* 15.0 g, *radix aconiti* 10.0 g, *folium perillae* 10.0 g and *radix platycodi* 8.0 g as the medicinal herbs of antistress components via the procedure described in the Example <2–1>.

Example 3

Preparation of the Pharmaceutical Compositions of Antistress Agents; Capsule

After lyophilizing the herb tea which was prepared by the Example <1–1> to <1–7>, the capsule of the antistress composition of the present invention was prepared by adding vehicle to the lyophilized herb tea and adjusting the weight of the capsule to 222 mg per one capsule.

Example 4

Preparation of the Pharmaceutical Compositions of Antistress Agents; Soft Capsule After lyophilizing the herb tea which was prepared by the Example <1–1> to <1–7>, the soft capsule of the antistress composition of the present invention. was prepared by adding soft vehicle to the lyophilized herb tea and the weight of the capsule was 324.3 mg per one capsule.

Example 5

Preparation of the Pharmaceutical Compositions of Antistress Agents; Liquid Formulation After solubilizing the herb tea which was prepared by the Example <1–1> to <1–7> by adding vehicle, the liquid formulation of the antistress composition of the present invention was prepared by adding purified water to the final volume 10 l as the customary method of liquid formulation.

Example 6

Preparation of the Pharmaceutical Compositions of Antistress Agents; Powders

After drying the herb tea which was prepared by the Example <1–1> to <1–7> by adding vehicle, the powders of the antistress composition of the present invention was prepared by the customary method of powder and adjusting the weight of powder to 1,000 mg for one pack.

Experimental Example 1

Preparation of Experimental Animal, Injection of Medicinal Herb and Appliance of Stress Well-educated organisms were selected and used after performing Morris water maze test (Redish, A. D. and Touretzky, D. S., The role of the hippocampus in solving the Morris water maze. Neural computation, 10 : 73–111, 19998; Moriguchi, T., Saito, H., and Nishiyama, N., Aged garlic extract prolongs longevity and improves spatial memory deficit in sequence-accelerated mouse. Bio. Pham. Bull., 19:305–307, 1996) to 7-weeks ICR male mouse (Korean experimental animal) and the experiments were performed as following 4 groups after they were separated to the control groups, which were not administered, and the experimental groups, which were administered with the herb tea extracts of the Example <1–1> to <1–7> and they were separated again to groups which were given stress or groups which were not given stress.

1) Control groups which were not administered with the herb tea extracts and were not given stress(Cont-Not),
2) Control groups which were not administered with the herb tea extracts and were given stress(Cont-Stress),
3) Experimental groups which were administered with the herb tea extracts and were not given stress(Treat-Not),
4) Experimental groups which were administered with the herb tea extracts and were given stress(Treat-Stress).

10–12 mice were used for each group and the herb tea extracts prepared by the Example <1–1> to <1–7> were orally administered by the dose of 8 g/kg/day per dried medicinal herb. The herb tea extracts were administered by storing solution in a freezer and equal amount of water was orally administered to the control group. For giving the stress, experimental animals were confined in the trays which were so small that experimental animals could barely enter and the stress were given by 15 min/day for 6 weeks. Administering the herb tea extracts and giving stress were performed in the same period, and 6 weeks later, all the animals were anesthetized with ether and the various intestinal organs were removed from the body after the whole blood was collected with heparin-treated syringe in the rear vein. The collected blood was used for CBC count(complete blood cell count) and centrifuged to separate blood plasma at 10,000 rpm at 4° C. for 10 min(eppendorf 5402 centrifuge). The removed intestinal organs and the separated blood plasma were stored at −70° C.

Experimental Example 2

Education of Experimental Animals

In order to verify the memory power of experimental animals, they were educated by Morris water maze test. The cylindrical water tank of the diameter 120 cm was filled with water which sinks destination below the water level at about 5 mm, and milk 6 l was added not to show the destination. The sense of direction by eyesight was excluded by intercepting external light and using indirect illumination in the experimental room which had the water tank. The maximum swimming time was determined for 2 min 30 sec and if they couldn't find the destination for that time, they were educated to recognize the destination where was direct line in the sunk water tank by artificial landing for 5 sec. The education was performed for 20 times and the well-educated organisms were selected and used in animal experiment. After administering the herb tea extracts and giving stress for 6 weeks, the educated memory level before administering the herb tea extracts and giving stress was observed by performing Morris water maze test for 4 times.

The results were compared of the behaviour of final 4 times(17, 18, 19, 20) in the 20 times educations of well-educated organisms' with the behaviour 6 weeks later after administering herb tea extracts and giving stress. The time (sec) which was taken to arrive the destination and the frequency of finding the destination were compared. By performing t-test, ANOVA-test, Bonferroni multiple comparison and Fisher's least-significant-difference test of the each result, the difference of the each group or before/after administration was decided to have the meaning in case of $p<0.05$.

Experimental Example 3

Measurement of Weight Variation by Administration of Herb Tea Extracts and Appliance of Stress After experimental animals were educated by Morris water maze test for 20 times, the weight of each group was measured weekly for 6 weeks before/after giving stress by administering the herb tea extracts of the Example <1–1>.

TABLE 1

Weight variation of each group in proportion to administration period

| Administration period (week) | Cont-Not | Cont-Stress | Treat-Not | Treat-Stress |
|---|---|---|---|---|
| 0 | 37.76 ± 1.13 | 35.82 ± 0.73 | 36.95 ± 0.48 | 36.09 ± 0.72 |
| 1 | 37.11 ± 1.08 | 36.28 ± 0.87 | 37.60 ± 0.46 | 35.98 ± 0.56 |
| 2 | 37.73 ± 0.87 | 36.01 ± 0.75 | 38.08 ± 0.40 | 35.78 ± 0.63 |
| 3 | 38.79 ± 1.16 | 36.69 ± 0.95 | 38.80 ± 0.46 | 36.03 ± 0.63 |
| 4 | 40.32 ± 1.15 | 35.44 ± 0.64# | 39.63 ± 0.86* | 35.78 ± 0.82# |
| 5 | 41.27 ± 1.01* | 38.02 ± 0.95 | 39.75 ± 0.49** | 37.18 ± 0.61## |
| 6 | 41.19 ± 0.97* | 38.16 ± 0.91 | 39.83 ± 0.45** | 37.23 ± 0.49## |

Compared by Bonferroni multiple comparison,

Comparing with OW of each group *; p<0.05, **; p<0.01,

Comparing with Cont-Not in each week age #; p<0.05

Figure 1:
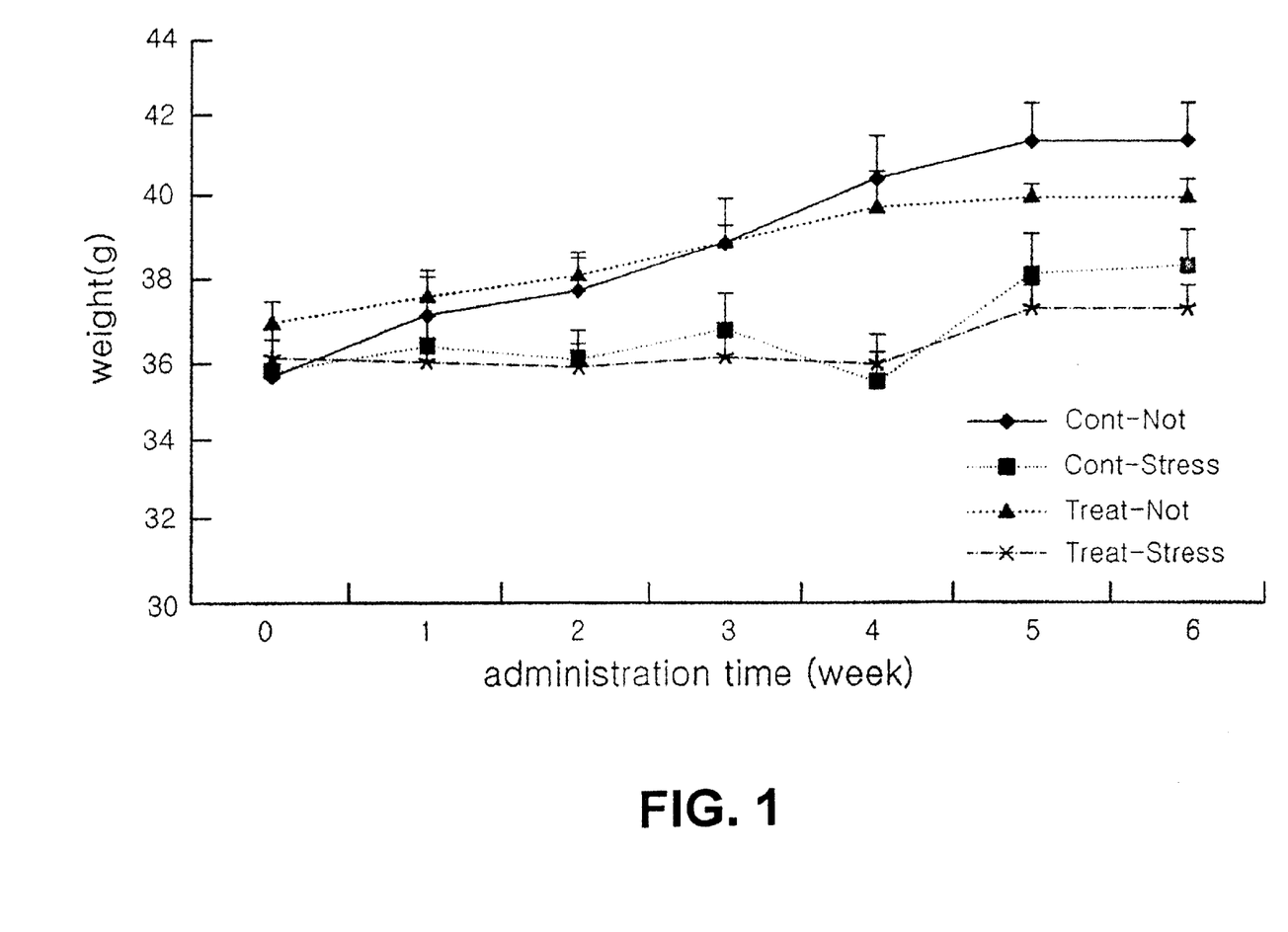
FIG. 1 shows weight variation in proportion to administration period after the medicinal herb extracts of antistress compositions of the present invention are administered to experimental animals, wherein Control group; the. group which are not administered with the medicinal herb tea extracts of antistress compositions of the present invention Experimental group; the group which are administered with the medicinal herb tea extracts of antistress compositions of the present invention ♦; the control group which are not given with stress ■; the control group which are given with stress ▼; the experimental group which are not given with stress ★; the experimental group which are given with stress

While weight increase which had meaning (p<0.05) was observed in 5 weeks in the group (Cont-Not) which were not given stress and weight increase which had meaning(p<0.05, p<0.01) was observed in 4 weeks after administering the herb tea extracts in the group (Treat-Not) by comparing before administration(0 week), the weight increase was not observed in the control group and experimental group(Cont-Stress and Treat-Stress) during the administration period of 6 weeks. These results showed that in normal state, the weight increased in proportion to week age and the administration of herb tea extracts didn't affect the weight increase in proportion to week age, and in stress-given state for 6 weeks, the weight increase was repressed in proportion to week age and the administration of herb tea didn't affect these repression phenomena. The herb tea extracts of the Example <1–2> to <1–7> showed the same results as the preceded results.

Experimental Example 4

Measurement of the Variation of Whole Blood Cell Number by Administering Herb Tea and Giving Stress The abnormality of immune system and hematopoietic function was decided by measuring whole blood cells which were collected from all the experimental animals after administering the herb tea extracts and giving stress. The number of leucocytes, lymphocytes, monocytes, granulocytes and RBC was measured from the blood of experimental animals which were given stress and administered with the herb tea extracts or were administered only of the herb tea extracts without stress. The amount of hemoglobin and capacity of RBC were compared and the results were shown in table 2.

TABLE 2

The variation of whole blood cell number in proportion to the administering herb tea extracts and the giving stress

| | Cont-not | Cont-Stress | Treat-not | Treat-Stress |
|---|---|---|---|---|
| Leucocyte | 4.00 ± 0.93 | 2.30 ± 0.47 | 2.77 ± 0.47 | 2.97 ± 0.37 |
| Lymphocyte | 3.28 ± 0.75 | 1.38 ± 0.18 | 2.11 ± 0.36 | 2.20 ± 0.27 |
| Monocyte | 0.40 ± 0.11 | 0.70 ± 0.43 | 0.51 ± 0.09 | 0.61 ± 0.10 |
| Granulocyte | 0.30 ± 0.12 | 0.30 ± 0.16 | 0.16 ± 0.06 | 0.15 ± 0.03 |
| RBC | 8.51 ± 0.23 | 8.55 ± 0.21 | 8.60 ± 0.12 | 8.93 ± 0.20 |
| Hemoglobin | 14.56 ± 0.34 | 14.51 ± 0.28 | 14.26 ± 0.19 | 14.76 ± 0.26 |
| Capacity ratio of RBC | 42.12 ± 1.07 | 42.67 ± 0.74 | 42.43 ± 0.51 | 43.94 ± 0.80 |

As described in the table 2, the measurement results of whole blood cell number showed that the immune system function and hematopoietic function were not varied in proportion to the administering herb tea extracts and the giving stress, and the herb tea extracts of the Example <1–2> to <1–7> showed the same results.

Experimental Example 5

Measurement of the Variation of Arrival Time by Administering Herb Tea Extracts and Giving Stress The present inventors showed the results of final 4 times in 20 times of Morris water maze test which were performed before administrating the herb tea extracts and 4 times of Morris water maze test which were performed 6 weeks later after administrating the herb tea extracts as time taken to arrive the destination in table 3 by using the herb tea extracts of the Example <1–1>.

TABLE 3

The variation of arrival time(sec) by administering the herb tea extracts and giving stress

| | Before administering herb tea extracts | 6 weeks later after administering herb tea extracts |
|---|---|---|
| Cont-not | 75.24 ± 8.59 | 69.95 ± 8.53 |
| Cont-stress | 61.41 ± 7.59 | 97.43 ± 8.18**$$ |
| Treat-not | 42.36 ± 6.02 | 49.55 ± 6.89##$$ |
| Treat-stress | 49.30 ± 6.29 | 54.77 ± 7.12 |

Comparing one week with 6 weeks of each group in t-test
**;p < 0.01,

Comparing Cont-Stress with Treat-Stress in t-test ##; p<0.01, Comparing one week with 6 weeks in ANOVA test $$; p<0.01, Comparing Cont-Stress with Treat-Stress in ANOVA test &&; p<0.01.

The time taken to find destination was 75.24±8.59 sec and 69.95±8.53 sec in the control group without stress, which showed no difference between before and 6 weeks later after administering the herb tea extracts in the results of Morris water maze test, but the time taken to find destination between before and 6 weeks later after administering the herb tea extracts had been increased very much to 61.41±7.59 sec and 97.43±8.18 sec in the group which were given stress for 15 min every day (p<0.01). On the other hand, the time taken to find destination was 42.36±6.02 sec and 49.55±6.89 sec in the experimental group without stress, which showed no difference between before and after administering the herb tea extracts, and the time was 49.30±6.29 sec and 54.77±7.12 sec, which showed no meaningful difference in the group which were given stress. In other words, ICR mouse memorized the destination where they were educated for 20 times 6 weeks later in normal state, but the educated memory power decreased very much by the 6 week-continued external physical stress. However, since the herb tea extracts which were administered with external physical stress repressed the memory decline which was induced by the stress. So it was verified that the antistress compositions of the present invention had the repressive effect of the memory failure which was induced by the stress and the recovering effect of memory power.

Experimental Example 6

Measurement of Frequency to Find Destination by Administering Herb Tea Extracts and Giving Stress Among the results of final 4 times of Morris water maze test which was performed for 20 times before administering the herb tea extracts and giving stress and the results of 4 times of Morris water maze test which was performed 6 weeks later after administering the herb tea extracts and giving stress, the frequencies of arriving the destination within 2 min 30 sec were showed in table 4.

TABLE 4 frequencies of arriving the destination by each group before/after administering the herb tea extracts

|  | Before administering herb tea extracts | 6 weeks later after administering herb tea extracts |
| --- | --- | --- |
| Cont-not | 3.18 ± 0.26 | 3.46 ± 0.16 |
| Cont-stress | 3.42 ± 0.15 | 2.42 ± 0.38* |
| Treat-not | 3.73 ± 0.14 | 3.55 ± 0.25 |
| Treat-stress | 3.70 ± 0.15 | 3.70 ± 0.15# |

Comparing before administration with 6 weeks later after administration by t-test,
*;p < 0.05
Comparing Cont-Stress with Treat-Stress by t-test,
;p < 0.05

In the results of measuring frequencies of arriving the destination of water tank within 2 min 30 sec which was standard time of Morris water maze test, the frequencies of finding the destination before and 6 weeks later after administering the herb tea extracts were not varied in the normal state, but in the stress group, the frequency of 3.42±0.15 before administering the herb tea extracts became the frequency of 2.42±0.38 6 weeks later after administering the herb tea extracts, which showed the frequencies of finding the destination decreased largely(p<0.05). On the other hand, in the experimental group, the frequencies of finding the destination before and after administering the herb tea extracts, which were same as that of normal state, were not varied in the group without stress, and the frequencies of finding the destination before and after administering the herb tea extracts were not varied in the group which were administered with the herb tea extracts and given stress, too. In addition, when the group (Cont-Stress) which was only given stress was compared with the group (Treat-Stress) which was administered with the herb tea extracts and given stress, the frequencies of finding the destination had no difference between the two groups before administering the herb tea extracts, but 6 weeks later after administering the herb tea extracts, the frequencies of finding the destination in the group which were administered with the herb tea extracts and given stress increased relative to the group which were only given stress(p<0.05). The herb tea extracts the Example <1–2> to <1–7> also showed same results.

Therefore, these results showed that the physical stress decreased the frequencies of finding the destination by declining the educated memory, but this memory failure could be normalized by administering the antistress compositions of the present invention.

As the results described in the above, it could be verified that experimental animals showed the decline of education power and memory power by the external physical stress, but the decline of education power and memory power was repressed by administering the antistress compositions of the present invention.

INDUSTRIAL APPLICABILITY

The present invention relates to an antistress composition containing various medical herbs as effective ingredients that relieve stress and repress memory failure.

Since the antistress composition of the present invention represents effective repression of memory failure as well as excellent preventive and curing effect to stress, and they can be used for preventing and treating stress.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An antistress composition containing a water extract or a honey extract of a mixture composed of *fructus hordei germintus* 2.0–40.0 g, *radix polygalae* 2.0–40.0 g, *poria holen* 2.0–40.0 g, *folium phyllostachys* 2.0–40.0 g, *germinated Glycine max (L.) Merr* 2.0–40.0 g, *rhizoma zingiberis* 2.0–40.0 g, *bulbos allii fistulosi* 2.0–40.0 g and *red pepper* 2.0–40.0 g.

2. The antistress composition according to claim 1, wherein the composition is in a form of herb tea, pill, tablet, capsule, soft capsule, liquid formulation, granule or powder.

3. The antistress composition according to claim 1, wherein the composition is the water extract.

4. The antistress composition according to claim 1, wherein the composition is the honey extract.

5. The antistress composition according to claim 1, wherein the composition is in a form of herb tea.

6. The antistress composition according to claim 1, wherein the composition is in a form of pill.

7. The antistress composition according to claim 1, wherein the composition is in a form of capsule.

8. The antistress composition according to claim 1, which is useful for preventing and treating stress or memory failure.

9. A method for preparing the composition of claim 1, comprising:
  a) soaking a mixture of the medicinal herbs comprised of *fructus hordei germintus* 2.0–40.0 g, *radix polygalae* 2.0–40.0 g, *poria holen* 2.0–40.0 g, *folium phyllostachys* 2.0–40.0 g, *germinated Glycine max (L.) Merr* 2.0–40.0 g and *rhizoma zingiberis* 2.0–40.0 g in water;

b) putting the soaked medicinal herbs of the step 1 into a pocket in order to obtain a water extract and adding the obtained water extract with *bulbos allii fistulosi* 2.0–40.0 g and *red pepper* 2.0–40.0 g into a water-containing, preheated extractor in order to obtain a herb tea; and, c) moving the extracted herb tea of the step 2 to a automatic package machine and packing the extracted herb tea in a predetermined amount with the automatic package machine.

10. A method for preparing the composition of claim 1, comprising:

a) preparing a mixture of medicinal herbs by mixing and powdering *fructus hordei germintus* 2.0–40.0 g, *radix polygalae* 2.0–40.0 g, *poria holen* 2.0–40.0 g, *folium phyllostachys* 2.0–40.0 g, *germinated Glycine max (L.) Merr* 2.0–40.0 g, *rhizoma zingiberis* 2.0–40.0 g, *bulbos allii fistulosi* 2.0–40.0 g and *red pepper* 2.0–40.0 g;

b) slowly heating honey until the honey becomes yellow after heating and filtering the honey for several times;

c) adding the mixture of medicinal herbs of the step 1 to the honey and kneading the medicinal herbs-added honey into dough;

d) molding the dough of the step 3 into pill; and, e) sealing up and storing the pill of the step 4 in the shaded and cold place after drying in the cold and dried place.

11. Health food which comprising the antistress composition of claim 1.

12. The health food of claim 11, which is useful for preventing and treating stress or memory failure.

* * * * *